United States Patent [19]

Haas

[11] Patent Number: Plant 5,829

[45] Date of Patent: Dec. 16, 1986

[54] OLIVE TREE, "HAAS IMPROVED MANZANILLO"

[76] Inventor: Alfred Haas, 440 W. Citrus Ave., Lindsay, Calif. 93427

[21] Appl. No.: 693,257

[22] Filed: Jan. 22, 1985

[51] Int. Cl.[4] ..... A01H 5/03

[52] U.S. Cl. ..... Plt./33

[58] Field of Search ..... Plt./33

*Primary Examiner*—Robert E. Bagwill

*Attorney, Agent, or Firm*—Worrel & Worrel

[57] ABSTRACT

An olive tree particularly characterized by its similarity to the Manzanillo olive tree of which it is a sport and from which it is distinguished by producing larger fruit which is more nearly spherical having smaller pits, and smaller leaves.

1 Drawing Figure

BACKGROUND OF THE NEW VARIETY

The present invention relates to a new and distinct variety of olive tree, to be known as the "Haas Improved Manzanillo", substantially as herein shown and described, characterized particularly as to novelty by bearing fruit which has an improved flesh to pit ratio as compared with that of known commercially grown olive trees.

PRIOR ART

In compliance with 37 C.F.R. §1.56, §1.97 and §1.98, the closest prior art known to the applicant are several unpatented varieties of olive trees of well known characteristics. The present variety olive tree is easily distinguished from the common, unpatented commercial varieties of olive trees, "Sevillano", "Ascolano", "Barouni" and "Obliza", sometimes collectively known as "Queens". It has a smaller fruit size and a much smaller pit size, as compared with the Queens. There are also other obvious differences, including leaf size, which is markedly smaller in the present variety.

Such variety is distinguished from the variety "Allegre" by bearing larger fruit and having much larger flesh to pit ratio of the present variety.

Further, the present variety is readily distinguished from the patented variety "Regina" Olive Tree (U.S. Plant Pat. No. 1,521) by the present variety's much smaller pit size and its much higher flesh to pit ratio. Still further, the shape of its fruit is more nearly round than ovoid and it has shorter, broader leaves. Additionally, the subject variety has shorter leaf internodes than the "Regina" Olive Tree.

The present variety is distinguished from the "Manzanillo" (unpatented), which it most clearly resembles, by the axillary angle, the angle between the branch and adjacent twig. In the subject variety, this angle averages 147.7° while the angle in the Manzanillo variety averages 165.8°. These angles were obtained by measuring ten specimens of each variety and determining that the standard deviation of the subject variety is 6.68°, and that of the Manzanillo variety is 4.51°, thereby distinguishing the two varieties by the well known statistical methods. The present variety is further distinguished from the "Manzanillo" variety in the order of blooming of the two varieties. The subject variety blooms from five to seven days later than the "Manzanillo". The subject variety blooms from May 15 to May 30, with full bloom being reached by May 22. The variety "Manzanillo" blooms from May 10 to May 25 with full bloom being reached by May 15. The present variety is further distinguished from the "Manzanillo" variety by the order of ripening of the two varieties. The subject variety ripens from 5 to 7 days later than the "Manzanillo" variety. The present variety is further distinguished from the "Manzanillo" variety by the flesh to pit ratio. These ratios for the two varieties were obtained by scraping all flesh from the pits of 10 fruits of similar size of each variety and weighing the accumulated flesh and the pits separately for each variety. The subject variety had 61 grams of flesh and 7½ grams of pit for a ratio of 8.1 to 1, while the variety "Manzanillo" had 54 grams of flesh and 13½ grams of pit for a ratio of 4 to 1.

ORIGIN AND ASEXUAL REPRODUCTION

The new variety of olive was discovered by me in 1972 as a chance seedling tree growing in my orange orchard adjoining my olive orchard (Manzanillo variety) located at the southeast corner of Road 212 and Avenue 216 near Lindsay, Calif., in Tulare County. The superiority of the new variety was not recognized until 1981 as the tree approached maturity.

The new variety was asexually reproduced by me at my olive orchard designated above in Lindsay, Calif., by rooting leaf cuttings of the new variety as well as by grafting hardwood scions onto trees of various olive rootstock. The fruit and tree characteristics of the resultant progeny in all cases proved identical with the new variety.

BRIEF DESCRIPTION OF THE DRAWING

The drawing is a colored photograph of typical leaves, and typical fruit in various stages of maturity showing pits and pit wells and providing a measuring scale for dimensional comparisons.

SUMMARY OF THE NEW VARIETY

The subject variety of olive tree is characterized by having the general characteristics of the "Manzanillo" variety but having the important distinctions of having a larger fruit, a smaller pit and which blooms and matures five to seven days later.

The leaf internodes of the twigs decrease in length from the base to the apical end. The leaf internodes of the subject variety are only slightly more than one-half the length of the "Manzanillo". This makes for a shorter, stockier limb structure which may be of advantage in mechanical harvesting.

BACKGROUND OF THE NEW VARIETY

In olives, the fruit for picking or processing is picked at less than full maturity for nearly all processes and is, at the time, inedible. The fruit is then made edible by applying a selected standard method of processing olives, such as by soaking in lye. Much of the cured olives are then pitted mechanically and some of the resulting fruit is then stuffed with capers, nuts, pimiento, and other edible materials. It is very desirable that the olive have a small pit and a large amount of flesh. Small olives frequently have a relatively large pit. For example, the small size, "petite", is only of limited use in processing or pitting and it is usually an economic loss to the grower.

The subject variety has very few "petites" while the variety "Manzanillo" frequently has 10% or even 20% "petites".

Nearly all olives are green in color when picked and the resultant color of the cured olive, be it black, gray, or various shades of green, is determined by the method used in curing the fruit.

DETAILED DESCRIPTION

The following description provides the botanical details of the subject variety olive tree grown under the ecological conditions prevailing in the San Joaquin Valley of California under normal cultural practices. The color definitions are as set forth in Maerz and Paul, *Dictionary of Color,* except where set forth in common terminology.

TREE

Size: The tree is moderately dwarfed when compared with the standard Manzanillo (unpatented) variety.

Shape: Has a normal, ball shape which is easily controlled by pruning. The dwarfing tendency reduces harvest picking costs. Trees are preferably artificially shaped to vase-form for improved pollination, ventilation, admission of sunlight, and harvesting convenience.

Productivity: Very good, with fruit born in clusters.

Regularity of bearing: Has slight tendency to alternate bearing.

Trunk:

*Diameter in relation to length.*—7 year old tree has a 5 inch (12.7 cm.) diameter; 3 year old tree has a 2 inch (5.08 cm.) diameter. Length of trunk determined by pruning. If not pruned, this plant develops as a multi-trunked bush.

Surface characteristics: Mature bark is smooth.

Branches:

*Size.*—Depending upon age, from ¼ inch (0.63 cm.) to more than 3 inches (7.62 cm.). Branches of same age are shorter and stiffer than Manzanillo.

Color: Ashy Gray Bark maturing to Gray at three years.

Lenticels:

*Number.*—Relatively few and irregularly spaced.

*Size.*—Small, 1/64 inch (0.04 cm.), length twice width, ovate in shape, not round.

Leaves:

*Size.*—Smaller than Manzanillo.

*Length.*—1.54 inches (3.91 cm.).

*Width.*—0.43 inches (1.09 cm.).

*Shape.*—Lanceolate.

*Color.*—Upperside — Plate 23, L-12; Underside — Plate 20, C-1, Eucalyptus Green.

*Marginal form.*—Smooth.

Petiole:

*Length.*—⅛ inch (0.32 cm.).

*Thickness.*—1/16 inch (0.16 cm.).

Stem glands: None.

Stipules: None.

Flower buds: Normal and typical of olive varieties.

Flowers:

*Dates of bloom.*—May 15 to May 30.

*Size.*—Approximately 3/16 inch (0.41 cm.) to ¼ inch (0.63 cm.) at full bloom.

*Color.*—White.

*Anthers.*—Large, yellow.

FRUIT

Maturity: Suitable for picking October 1.

Size:

*Uniformity.*—Good, very few fruit less than 11/16 inch (1.74 cm.) medium.

*Diameter.*—¾ inch (1.90 cm.) to ⅞ inch (2.22 cm.).

*Length.*—Large, ⅞ inch (2.22 cm.) to 1 inch (2.54 cm.).

Form: Uniformity — Good.

Suture: None.

Stem cavity: Small.

Base: Small.

Pistil point: Very slight point at pistil end.

Stem:

*Length.*—Varys to 2½ inches (6.35 cm.).

*Caliper.*—1/16 inch (0.16 cm.) to 3/64 inch (0.12 cm.).

Skin:

*Thickness.*—Thin.

*Texture.*—Smooth.

*Tendency to crack.*—None.

*Color.*—Immature — Plate 20, J-5 Absinthe Green; Light Reddish — Plate 6, D-11, Plantation — Deeper Red — Plate 8, J-6, Briarwood — Black — Plate 48, L-12.

*Pubescence.*—None.

Flesh:

*Color.*—White, Immature — Plate 18, C-1; Mature — Plate 10, C-1, Marguerite Y.

*Surface of pit cavity.*—White.

*Color of pit well.*—White.

*Texture.*—Smooth, firm.

*Fibers.*—None.

*Ripening.*—Even.

*Eating Quality.*—Canning quality excellent.

Stone: Semi-free.

*Fibers.*—Few.

*Size.*—Length — 5/8 inch (1.58 cm.).

*Form.*—Elliptical (prolate spheroid).

*Base.*—Rounded to slight point.

*Sides.*—Symmetrical.

*Ridges.*—Normal for olives.

*Size of grooves.*—1/64 inch (0.04 cm.) deep.

*Color.*—Plate 11, J-6, Honeysweet.

*Splitting tendency.*—Slight to none.

Use: For canning as black ripe or green ripe, for Spanish style, plain or spiced, for home cure style.

Keeping quality: Good.

Shipping quality: Excellent.

Resistance to disease: Normal for peacock spot, better than normal for olive knot. Verticillium and phytophthora unknown.

Although the new variety of olive tree possesses the described characteristics as a result of the growing conditions in Tulare County, Calif., in the central part of the San Joaquin Valley, it is to be understood that variations of the usual magnitude in characteristics incident to growing conditions, fertilization, pruning and pest control are to be expected.

Having thus described and illustrated my new variety of olive tree, what I claim as new and desire to secure by Plant Letters Patent is:

1. A new and distinct variety of olive tree characterized by bearing fruit which is larger than that of the well known Manzanillo (unpatented) variety, but smaller than that of the Sevillano (unpatented) or Ascolano (unpatented) and being most nearly similar to the Manzanillo, from which it is further distinguished by having smaller leaves, producing fruit which is more nearly spherical, which fruit has smaller pits, and ripens five to seven days later than that of the Manzanillo and has an improved flesh to pit ratio.

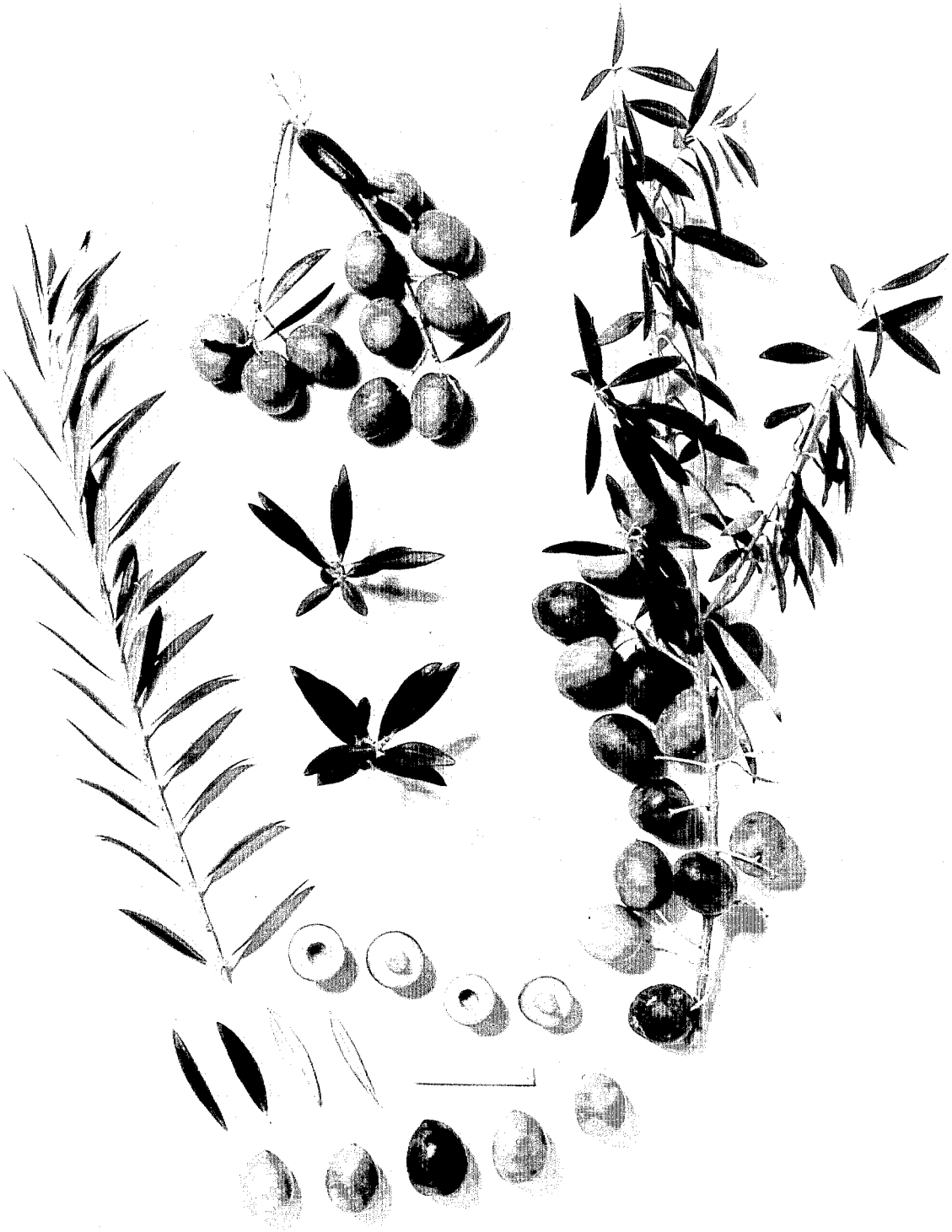

* * * * *